United States Patent [19]

Carcano et al.

[11] Patent Number: 5,180,590
[45] Date of Patent: Jan. 19, 1993

[54] PROCESS FOR THE PREPARATION OF ANTI-INFLAMMATORY PHARMACEUTICAL AGENTS WITH AN IBUPROFEN BASE, WITH ELIMINATION, IN SOLUTION, OF THE BITTER TASTE, BURNING OF THE THROAT AND INTESTINAL TOXICITY

[75] Inventors: Mario Carcano, Vezia; Massimo Costa, Arzo, both of Switzerland

[73] Assignee: Aesculapius-Pharma S.A., Mezzovico, Switzerland

[21] Appl. No.: 372,633

[22] Filed: Jun. 13, 1989

[30] Foreign Application Priority Data

Jul. 12, 1988 [CH] Switzerland .......................... 2647/88

[51] Int. Cl.⁵ .......................... A61K 9/46; A61K 31/19
[52] U.S. Cl. ..................................... 424/466; 514/570
[58] Field of Search .......................... 514/557, 570, 298; 424/466

[56] References Cited

U.S. PATENT DOCUMENTS 4,806,358  2/1989  Khan .................................... 514/520
5,055,306  10/1991  Barry .................................... 424/466

FOREIGN PATENT DOCUMENTS 0313328  4/1989  European Pat. Off. .

OTHER PUBLICATIONS

Barry et al., "Sustained-release granular . . ." CA 112(6) 62596k (1990).

Primary Examiner—C. Warren Ivy
Assistant Examiner—Celia Chang
Attorney, Agent, or Firm—Young & Thompson

[57] ABSTRACT

Anti-inflammatory pharmaceutical compositions with an ibuprofen base which eliminate the bitter taste, the burning in the throat and the topical toxicity at the level of the intestinal wall when their effervescent aqueous solutions are taken. The proportions among the main ingredients of each dose are the following: ibuprofen, 200 to 800 mg or ibuprofen sodium salt, 221.3 to 885.2 mg; sodium bicarbonate, 2.100 to 8.402 g; and citric acid, 0.450 to 1.800 g.

6 Claims, No Drawings

PROCESS FOR THE PREPARATION OF ANTI-INFLAMMATORY PHARMACEUTICAL AGENTS WITH AN IBUPROFEN BASE, WITH ELIMINATION, IN SOLUTION, OF THE BITTER TASTE, BURNING OF THE THROAT AND INTESTINAL TOXICITY

Ibuprofen is well-known as a valuable pharmaceutical agent, endowed with analgesic and antipyretic properties; its use is becoming quickly and broadly accepted and, in appropriate doses, is now classified among the safe pharmaceutical agents not requiring a prescription (over-the-counter product), at least up to certain well-defined dosages.

Ibuprofen, or (±)-2-(p-isobutylphenyl)-propionic acid (synonym: (±)-p-isobutylhydrotropic acid) has the following structural formula:

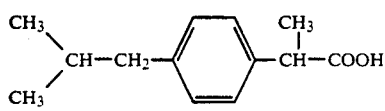

It was described by T. Shiori and N. Kawai (J. Org. Chem. 43, 2936 (1978)) and by J. T. Pinhey and B. A. Rowe (Tetrahedron Letters 21, 965 (1980). The pharmacological research conducted by Adams et al. is described in Arch. Pharacodyn. Ther. 178, 115 (1969). A summary publication of the data relating to ibuprofen was published in 1975 (cf. L. Cavallini and G. Lucchetti —Gazz. Med. It. 134, 7 (1975). Ibuprofen is claimed in British patent—BP 971,700 (1964) corresponding to U.S. Pat. Nos. 3,228,831 and 3,385,886 of 1966 and 1968 assigned to the Boots Pure Drug Company. Ibuprofen is an exceptional nonsteroidal anti-inflammatory agent, with very low systemic toxicity and provided with interesting analgesic and antipyretic properties. This pharmaceutical agent compares favorably with acetylsalicylic acid itself over which it has the advantage of less topical toxicity, at the level of the gastrointestinal tract. However, like aspirin, in the case of particularly sensitive patients, there are the phenomena of toxicity at the level of the intestinal wall, especially when the pharmaceutical agent is administered in solid, monolithic formulations (sugar-coated pills and tablets).

Use of ibuprofen for treatment of inflammatory conditions, for example, rheumatoid arthritis, swelling of the joints, morning stiffness of the joints, but even more for those accompanied by pain and elevation of temperature, would require having liquid pharmaceutical forms, easy to swallow even by elderly patients whom the very arthritic phenomena make particularly awkward.

The making of a formulation of ibuprofen in solution is not possible today because of the bad taste of the product and in particular because of the bitter taste and the unbearable burning in the throat which appears at the moment of taking it and remains for an extended period.

Even the attempt to prepare effervescent palatable tablets so far has not produced satisfactory results. In European patent EP 0228164 A 2 Jul. 8, 1987), assigned to the Boots Co. of Nottingham (U.K.) effervescent tablets are described and claimed in which the ibuprofen is present in undissolved form in suspension, the latter is promoted by particular excipients, such as sodium lauryl sulfate, polyisoethylene sorbitan monolaurate and polymers insoluble in water. The fact that the ibuprofen is present in suspension in the solid state, undissolved in water, prevents the elimination of the above-mentioned organoleptic properties: the product, in effervescent aqueous suspension, is actually completely unpalatable and is practically impossible to use.

DESCRIPTION OF THE INVENTION

Research on tablets and effervescent granules in general and on those that contain ibuprofen as active ingredient in particular has led, according to the invention, to very satisfactory although unforeseeable results. Actually, by operating with a suitable ratio between citric acid/sodium bicarbonate and ibuprofen it was possible, also thanks to the use of suitable equipment, to prepare effervescent granules and tablets which, placed in water—100/200 ml—develop carbon dioxide and provide a clear solution.

In particular 200 mg of ibuprofen, 2100 mg of sodium bicarbonate and 500 mg of citric acid, suitably mixed and granulated dry in suitable equipment (fluidized bed), optionally compressed to form tablets of 4.5 grams, dissolve quickly and completely in 100/200 ml of water at ambient temperature. That a true and proper solution is involved, obviously obtained by salification of the ibuprofen, can be easily proven by filtering the solution on filter paper and measuring the ibuprofen content (sodium salt) in the aqueous phase, a content that is greater than 98% of theory.

The solution obtained after total decomposition of the tablets—necessary time from 30 to 90 seconds—the taste of the whole is tolerable: in particular it is not bitter and does not cause irritation of the throat. Obviously the granules and tablets can be obtained also by using the ibuprofen sodium salt. In this case, 221.3 mg of ibuprofen sodium salt is suitably mixed and granulated with 2035 mg of sodium bicarbonate and 540 mg of citric acid. The dosage of 200 mg is that of election for use of the pharmaceutical agent as an over-the-counter product. However, it is possible to compress greater and multiple amounts of the basic dosage to obtain formulations with a content up to 800 mg of ibuprofen.

Obviously, it is possible to dissolve two or more tablets in the same volume of water of 100/200 ml, obtaining a solution having good palatability.

Flavoring of the granules or tablets makes it possible to obtain a product of exceptional quality. Particularly effective flavors are mint 3813, anise 3812, but this is not a limitation, other essences also being effective. Finally, but not last, with the administration of the active ingredient in solution a faster pharmacodynamic action and certainly a faster onset are obtained in comparison with those obtainable with traditional (monolithic) tablets. This aspect becomes particularly important in the use of ibuprofen as a painkiller.

Theoretically local tolerability, already good per se, is increased further by using dilute solutions, incapable of producing high topical concentrations of the active ingredient.

EXAMPLES

| 1. Ibuprofen tablets (200 mg of ibuprofen per tablet of about 4.5 g) | |
|---|---|
| Ibuprofen | 13.33 kg |
| NaCl | 3.00 kg |
| NaHCO$_3$ | 140.00 kg |

| 1. Ibuprofen tablets (200 mg of ibuprofen per tablet of about 4.5 g) | |
|---|---|
| Citric acid | 30.30 kg |
| Na saccharin | 3.00 kg |
| Dextrose | 107.91 kg |
| Na glutamate | 0.3 kg |

Transfer these products in the granulator with fluidized bed, then proceed to granulation with H₂O, dry and transfer to tabletmaking machines. The granulate is compressed, tablets being obtained 25 mm in diameter with an average weight of 4.5 g.

| 2. Ibuprofen tablets (200 mg of ibuprofen per tablet of about 4.5 g) | |
|---|---|
| Ibuprofen | 13.33 kg |
| NaCl | 3.00 kg |
| NaHCO₃ | 140.00 kg |
| Citric acid | 30.00 kg |
| Na saccharin | 3.00 kg |
| Dextrose | 107.91 kg |
| Mint 3813 flavor | 2.40 kg |
| Anise 3812 flavor | 0.60 kg |
| Na glutamate | 0.30 kg |

These products are put into a granulator with fluidized bed, then granulation with H₂O and drying are performed, finally the granules are transferred to the rotary tabletmaking machines. Tabletmaking is performed, tablets 25 mm in diameter with a weight of 4.5 g being obtained.

| 3. Ibuprofen granules in packets | |
|---|---|
| Ibuprofen | 13.33 kg |
| NaCl | 3.00 kg |
| NaHCO₃ | 140.00 kg |
| Citric acid | 30.30 kg |
| Na saccharin | 3.00 kg |
| Dextrose | 107.91 kg |
| Na glutamate | 0.3 kg |

Place the weighed material in a granulator with fluidized bed, then proceed to spraying with H₂O. When the granules are obtained, the product is analyzed, finally it is transferred to the packaging machine filling the packets with 4.5 g of granules.

| 4. Ibuprofen granules in packets | |
|---|---|
| Ibuprofen | 13.33 kg |
| NaCl | 3.00 kg |
| NaHCO₃ | 140.00 kg |
| Citric acid | 30.00 kg |
| Na saccharin | 3.00 kg |
| Dextrose | 107.91 kg |
| Mint 3813 flavor | 2.40 kg |
| Anise 3812 flavor | 0.60 kg |
| Na glutamate | 0.30 kg |

Granulate this mixture with a granulator with fluidized bed with H₂O, dry and analyze the granules. The product is transferred to packaging machines, then the packets are filled with 4.5 g of granules.

| 5. Tablets of ibuprofen sodium salt 200 mg | |
|---|---|
| Ibuprofen sodium salt | 14.75 kg |
| NaCl | 3.00 kg |
| NaHCO₃ | 134.90 kg |
| Citric acid | 30.30 kg |
| Na saccharin | 3.00 kg |
| Dextrose | 107.91 kg |
| Mint flavor | 2.40 kg |
| Anise flavor | 0.60 kg |
| Na glutamate | 0.30 kg |

Granulate this mixture with H₂O in a granulator with fluidized bed; when the granules are obtained, analytically check the distribution, finally transfer the product to rotary tabletmaking machines, make the tablets, obtaining tablets 25 mm in diameter and with a weight of 4.5 g.

| 6. Tablets of ibuprofen sodium salt 200 mg | |
|---|---|
| Ibuprofen sodium salt | 14.75 kg |
| NaCl | 3.00 kg |
| NaHCO₃ | 135.50 kg |
| Citric acid | 30.00 kg |
| Na saccharin | 3.00 kg |
| Dextrose | 107.91 kg |
| Na glutamate | 0.30 kg |

Granulate this mixture with a granulator with a fluidized bed, spray with H₂O. When the granules are obtained, the product is analyzed, finally it is transferred to tabletmaking machines. It is compressed, obtaining tablets 25 mm in diameter with an average weight of 4.5 g.

| 7. Tablets of ibuprofen sodium salt 200 mg (in packets) | |
|---|---|
| Ibuprofen sodium salt | 14.75 kg |
| NaCl | 3.00 kg |
| NaHCO₃ | 134.90 kg |
| Citric acid | 30.00 kg |
| Na saccharin | 3.00 kg |
| Dextrose | 107.91 kg |
| Mint flavor | 2.40 kg |
| Anise flavor | 0.60 kg |
| Na glutamate | 0.30 kg |

Granulate with a granulator with fluidized bed, spraying with H₂O. When the drying is completed, analyze the granules, then transfer them to packaging machines. The packets are filled with 4.5 g of granules.

| 8. Tablets of ibuprofen sodium salt 200 mg (in packets) | |
|---|---|
| Ibuprofen sodium salt | 14.75 kg |
| NaCl | 3.00 kg |
| NaHCO₃ | 135.50 kg |
| Citric acid | 30.30 kg |
| Na saccharin | 3.00 kg |
| Dextrose | 107.91 kg |
| Na glutamate | 0.30 kg |

Transfer the products into a granulator with fluidized bed, then proceed with granulation with H₂O. After drying and analytical checking of the distribution, the product is transferred to the packaging machines. The packets are filled with 4.5 g of granules.

We claim:
1. An anti-inflammatory pharmaceutical composition, consisting essentially of the following ingredients in intimate admixture: 200 to 800 mg ibuprofen or 221.3 to

885.2 mg ibuprofen sodium salt, 2.100 to 8.402 g sodium bicarbonate. and 0.450 to 1.800 g citric acid.

2. The composition according to claim 1, containing 200 to 800 mg ibuprofen.

3. The composition according to claim 1, containing 221.3 to 885.2 mg ibuprofen sodium salt.

4. An effervescent solution containing the composition according to claim 2 dissolved in water.

5. An effervescent solution containing the composition according to claim 3 dissolved in water.

6. A tablet comprising the composition according to claim 1 in compressed form.

* * * * *